US012594413B2

(12) United States Patent
Callahan et al.

(10) Patent No.: US 12,594,413 B2
(45) Date of Patent: Apr. 7, 2026

(54) AUTO SHUT OFF MALE LUER FITTING

(71) Applicant: CareFusion 303, Inc., San Diego, CA (US)

(72) Inventors: Ryan Callahan, Long Beach, CA (US); Todd Oda, Torrance, CA (US); George Mansour, Diamond Bar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 976 days.

(21) Appl. No.: 17/703,828

(22) Filed: Mar. 24, 2022

(65) Prior Publication Data

US 2022/0313979 A1 Oct. 6, 2022

Related U.S. Application Data

(60) Provisional application No. 63/168,177, filed on Mar. 30, 2021.

(51) Int. Cl.
*A61M 39/26* (2006.01)
*A61M 39/10* (2006.01)

(52) U.S. Cl.
CPC ............ *A61M 39/26* (2013.01); *A61M 39/10* (2013.01); *A61M 2039/1033* (2013.01); *A61M 2039/263* (2013.01)

(58) Field of Classification Search
CPC .... A61M 2039/267; A61M 2039/1027; A61M 2039/2433; A61M 2039/263;
(Continued)

(56) References Cited

U.S. PATENT DOCUMENTS

| | | | | |
|---|---|---|---|---|
| 4,143,853 | A | 3/1979 | Abramson | |
| 7,044,441 | B2 * | 5/2006 | Doyle .................. | A61M 39/26 251/149.6 |
| 2006/0192164 | A1 * | 8/2006 | Korogi ................. | A61M 39/26 251/149 |

FOREIGN PATENT DOCUMENTS

| | | |
|---|---|---|
| EP | 1371894 A1 | 12/2003 |
| JP | 2008522729 A | 7/2008 |

(Continued)

OTHER PUBLICATIONS

International Preliminary Report on Patentability from the International Preliminary Examining Authority for Application No. PCT/US2022/020427, dated May 25, 2023, 18 pages.
(Continued)

*Primary Examiner* — Kevin C Sirmons
*Assistant Examiner* — Alexandra Lalonde
(74) *Attorney, Agent, or Firm* — MASCHOFF BRENNAN

(57) ABSTRACT

A medical connector may include a body having an outer surface and an inner surface defining a lumen of the body, an inlet port defined at a proximal end of the body, and an outlet port defined at a distal end of the body. The medical connector may further include a compressible valve member comprising a normally closed slit and disposed in the lumen and extending through the inner surface and outer surface of the body to an exterior of the medical connector. The compressible valve member may be configured to compress radially inward to open the slit upon insertion of the body into a medical access device, and expand radially outward to close the slit upon disconnection of the body from the medical access device.

10 Claims, 5 Drawing Sheets

(58) Field of Classification Search
CPC .... A61M 2039/261; A61M 2039/1033; A61M
2039/2426; A61M 2039/266; A61M
2039/244; A61M 39/22; A61M 39/26;
A61M 39/10; A61M 39/045; A61M
2005/3128; A61M 5/347; A61B 5/150221
See application file for complete search history.

(56)                          References Cited

FOREIGN PATENT DOCUMENTS

| JP | 2008529680 A | 8/2008 |
|----|--------------|--------|
| JP | 4708352 B2 | 6/2011 |
| WO | WO-03018104 A2 | 3/2003 |

OTHER PUBLICATIONS

International Search Report and Written Opinion for Application
No. PCT/US2022/020427, dated Jul. 4, 2022, 13 pages.
Written Opinion from the International Preliminary Examining
Authority for Application No. PCT/US2022/020427, dated Mar. 1,
2023, 7 pages.
Japanese Office Action for Application No. 2023-552188, dated Oct.
24, 2025, 9 pages including translation.

* cited by examiner

AUTO SHUT OFF MALE LUER FITTING

CROSS-REFERENCE TO RELATED APPLICATIONS

This application claims the benefit of U.S. Provisional Application No. 63/168,177, filed Mar. 30, 2021, the entirety of which is incorporated herein by reference.

TECHNICAL FIELD

The present disclosure generally relates to medical fluid connectors and, in particular, to auto shut off male luer fittings which are designed to close the fluid path when disconnected from a medical access device.

BACKGROUND

Medical connections are widely used in fluid delivery systems such as those used in connection with intravenous fluid lines, blood access, hemodialysis, peritoneal dialysis, enteral feeding, drug vial access, etc.

Traditional medical connectors require the health care provider to exercise great care on connection or disconnection due to the likelihood of the drug remaining inside the connector or dripping, particularly on disconnection when the connectors are primed with fluid. Health care providers must also make sure to physically close all clamps to prevent a free flow leak state. Some female connectors are designed to push fluid in the throat of the connector to the surface during disconnection. While this is desirable for aseptic connectors to provide a swabbable surface, it can result in fluid drips from the device on disconnection. Other connectors use a membrane with a septum that can also allow fluids to escape the connector.

The description provided in the background section should not be assumed to be prior art merely because it is mentioned in or associated with the background section. The background section may include information that describes one or more aspects of the subject technology.

SUMMARY

What is needed is a connector for medical fluids that has standardized connections for use with existing medical connectors and also minimizes or eliminates drips on connection or disconnection. What is also needed is an auto shut off male luer connector which allows the clinician to simply disconnect without having to physically close all clamps to prevent a free flow leak state.

In accordance with various embodiments of the present disclosure, a medical connector may include a body having an outer surface and an inner surface defining a lumen of the body, an inlet port defined at a proximal end of the body, and an outlet port defined at a distal end of the body, and a compressible valve member. The compressible valve member may have a normally closed slit and be disposed in the lumen extending through the inner and outer surfaces of the body to an exterior of the medical connector. The compressible valve member may be configured to compress radially inward to open the slit upon insertion of the body into a medical access device. The compressible valve member may additionally be configured to expand radially outward to close the slit upon disconnection of the body from the medical access device.

In accordance with various embodiments of the present disclosure, a method of assembling a medical connector may include providing a connector body having an outer surface and an inner surface defining a lumen of the connector body. The method may further include positioning a compressible valve member having a normally closed slit in the lumen with an outer surface of the compressible valve member extending through the inner and outer surfaces of the connector body to an exterior of the medical connector.

In accordance with various embodiments of the present disclosure, a connector assembly may include a female luer comprising an outer surface and an inner surface defining a lumen of the female luer, and a male luer removably disposed at least partially in the lumen of the female luer. The male luer may include a body having an outer surface and an inner surface defining a lumen of the body, and a compressible valve member disposed in the lumen and extending through the inner and outer surfaces of the body. The compressible valve member may have an outer surface and an inner surface including a slit. The inner surface of the female luer may compress at least a portion of the outer surface of the compressible valve member to open the slit when the male luer is disposed in the female luer. Upon removal from the female luer, the compressible valve member may expand radially outward to close the slit.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
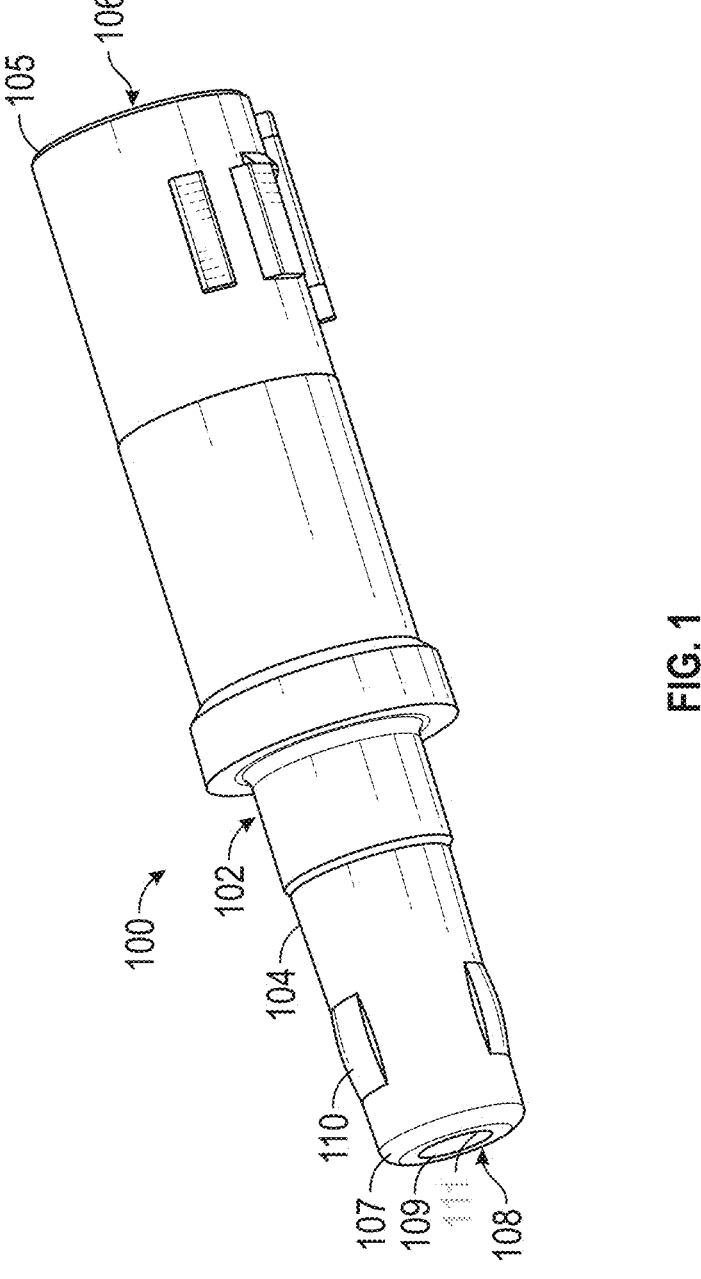
FIG. 1 illustrates a perspective view of a male luer medical connector for fluid delivery, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Various embodiments of the present disclosure are directed to providing a medical connector for minimizing fluid leakage resulting from accidental or inadvertent disconnection of the medical connector from a medical access device, e.g., a female luer or other needleless valve. Similar to currently existing medical connectors, male luer portions of the medical connector of the various embodiments of the disclosure described herein, may be inserted into a female luer of another needleless access device to create a fluid path between a fluid delivery mechanism and a patient. In order to avoid drips and leakage of medical fluids that may be harmful to health care providers or patients, the medical connector of the various embodiments described herein is designed to minimize or eliminate fluid drips or leakage upon connection of medical connector 100 with another access device, or particularly upon disconnection from another access device when both devices are primed with fluid.

According to various aspects of the present disclosure, the proximal end of the medical connector may include an inlet port that can be connected to fluid delivery sources or devices such as IV fluid bags, pumps or the like. In some embodiments, the medical connector may be a male luer of have a male luer portion having a body which is ISO compliant and interfaces with standard female luers or needleless access devices. As shall be described in further detail, the medical connector of the various embodiments described herein may differ from a traditional male luer by the inclusion of a compressible valve member including a normally closed slit. The compressible valve member may be disposed in the lumen of the medical connector extending through the inner and outer surfaces of the body to an exterior of the medical connector. In some embodiments, the compressible valve member may be configured to compress radially inward to open the slit upon insertion of the body into a medical access device. The compressible valve member may be configured to expand radially outward to close the slit upon disconnection of the body from the medical access device. Accordingly, the medical connector of the various embodiments described herein may advantageously prevent dripping or leakage of medical fluid, which is a common issue occurring upon disconnection of the currently existing medical connectors (e.g., male luer) from the medical access devices. Further advantageously, the auto shut off medical connector of the various embodiments described herein may allow the clinician to simply disconnect without having to physically close all clamps to prevent a free flow leak state.

FIG. 1 illustrates a perspective view of a male luer medical connector 100 for fluid delivery, in accordance with some embodiments of the present disclosure. As depicted, medical connector 100 may include a body 102. Body 102 may have an outer surface 104 and an inner surface 109 defining a lumen 111 of the body 102. The connector 100 may further include an inlet port 106 defined at a proximal end 105 of the body 102, and an outlet port 108 defined at a distal end 107 of the body 102. The inlet port 106 may be connected to fluid delivery sources or devices such as IV fluid bags, pumps or the like. As shall be described in further detail below with respect to at least FIGS. 5A and 5B, the distal end 107 including the outlet port 108 of medical connector 100 may be inserted into the female luer of another medical access device to create a fluid path 126 between the fluid delivery sources or devices and a patient. In some embodiments, the lumen 111 fluidly communicates the inlet port 106 and the outlet port 108, and forms a part of the fluid path between the fluid delivery sources or devices and the patient.

In some embodiments, inlet port 106 may accept male luer portions of other medical access devices and allows fluids to pass into fluid path 126. Accordingly, the proximal end 105 of the connector 100 may be in the form of a female luer portion, or any other type of inlet port, for example, a bond pocket or other connector, while remaining within the scope of the concepts described herein.

Figure 2A:
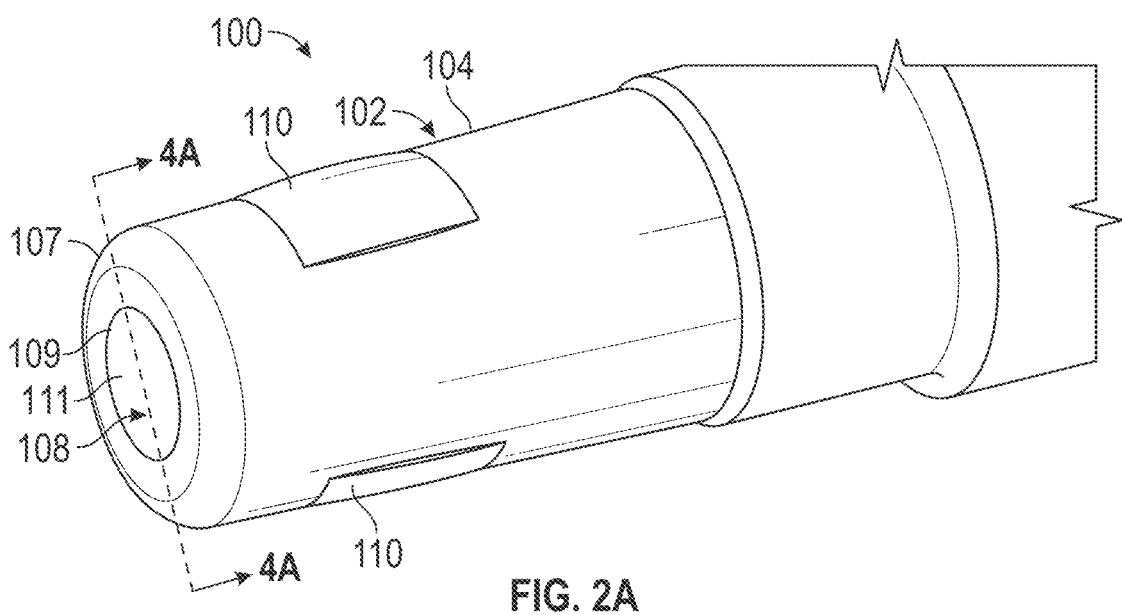
FIG. 2A illustrates a partial perspective view of a male luer medical connector with valve member in an open position, in accordance with some embodiments of the present disclosure.
Figure 2B:
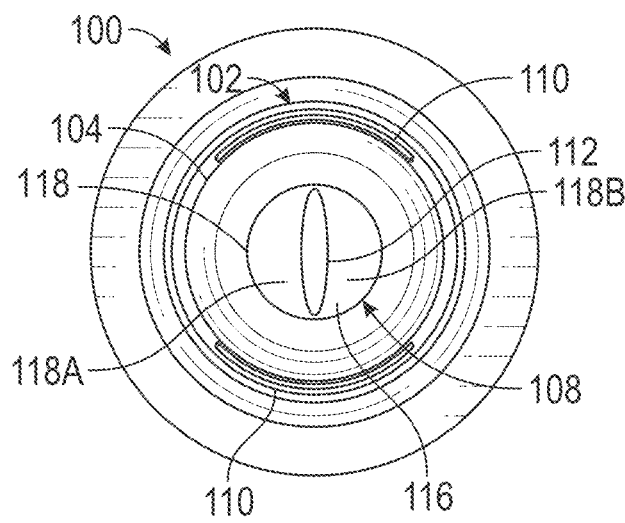
FIG. 2B illustrates a front planar view of the view of the male luer medical connector of FIG. 2A, in accordance with some embodiments of the present disclosure.
Figure 3A:
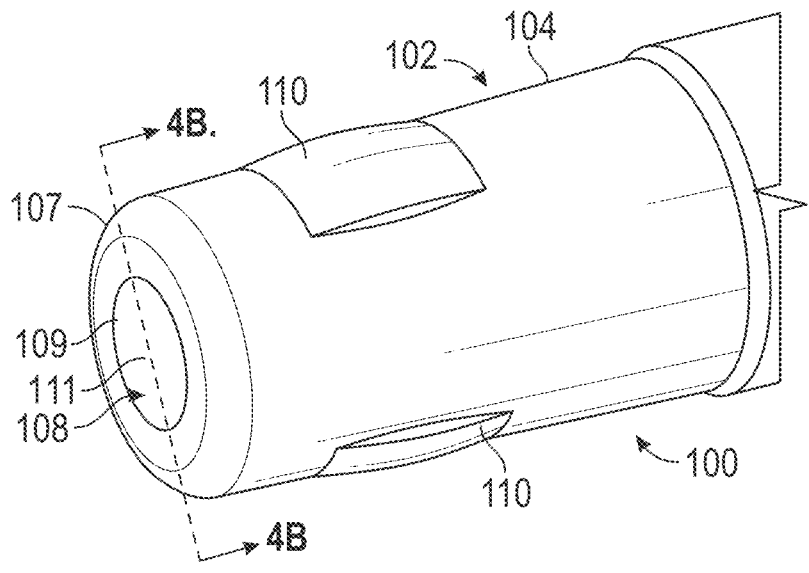
FIG. 3A illustrates a partial perspective view of a male luer medical connector with valve member in a closed position, in accordance with some embodiments of the present disclosure.
Figure 3B:
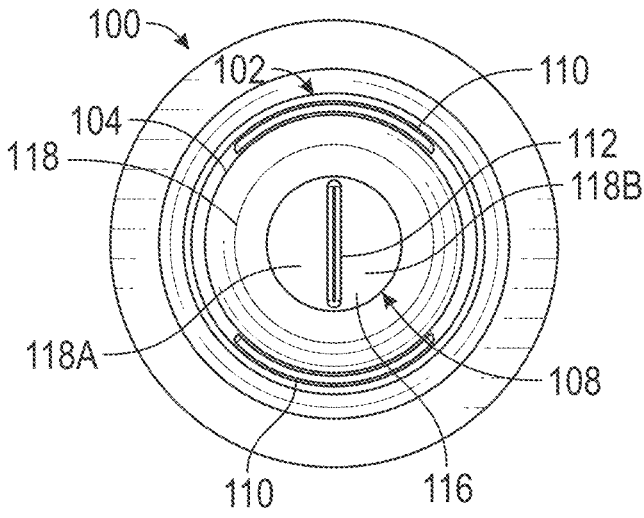
FIG. 3B illustrates a front planar view of the view of the male luer medical connector of FIG. 3A, in accordance with some embodiments of the present disclosure.

FIG. 2A illustrates a partial perspective view of a male luer medical connector 100 with valve member 116 in an open position, in accordance with some embodiments of the present disclosure. FIG. 2B illustrates a front planar view of the view of the male luer medical connector 100 of FIG. 2A, in accordance with some embodiments of the present disclosure. FIG. 3A illustrates a partial perspective view of a male luer medical connector 100 with valve member 116 in a closed position, in accordance with some embodiments of the present disclosure. FIG. 3B illustrates a front planar view of the view of the male luer medical connector 100 of FIG. 3A, in accordance with some embodiments of the present disclosure.

Referring to FIGS. 2A-3B, the connector 100 may further include a compressible valve member 116 disposed in the lumen 111. As depicted in FIGS. 2A and 2B, the compressible valve member 116 may extend through the inner and outer surfaces 109 and 104 of the body 102 to an exterior of the medical connector 100. In some embodiments, the compressible valve member 116 may be formed of or otherwise include an elastomeric material. In some embodiments, the elastomeric material may be silicone, Thermoplastic Polyurethane (TPU), or a combination thereof.

As further depicted in FIGS. 3A and 3B, the compressible valve member 116 may include a normally closed slit 112 that may be configured to selectively open and close the fluid path 126 between the fluid delivery sources or devices and the patient. In particular, as illustrated in FIGS. 2A and 3A, and as shall be described in further detail with respect to FIGS. 5A and 5B, the compressible valve member 116 may be configured to compress radially inward to open the slit 112 upon insertion of the body 102 into a medical access device 150. Further, as illustrated in FIGS. 2B and 3B, and as shall be described in further detail with respect to FIGS. 5A and 5B, the compressible valve member 116 may be configured to expand radially outward to close the slit 112 upon disconnection of the body 102 from the medical access device 150.

Figures 4A, 4B:
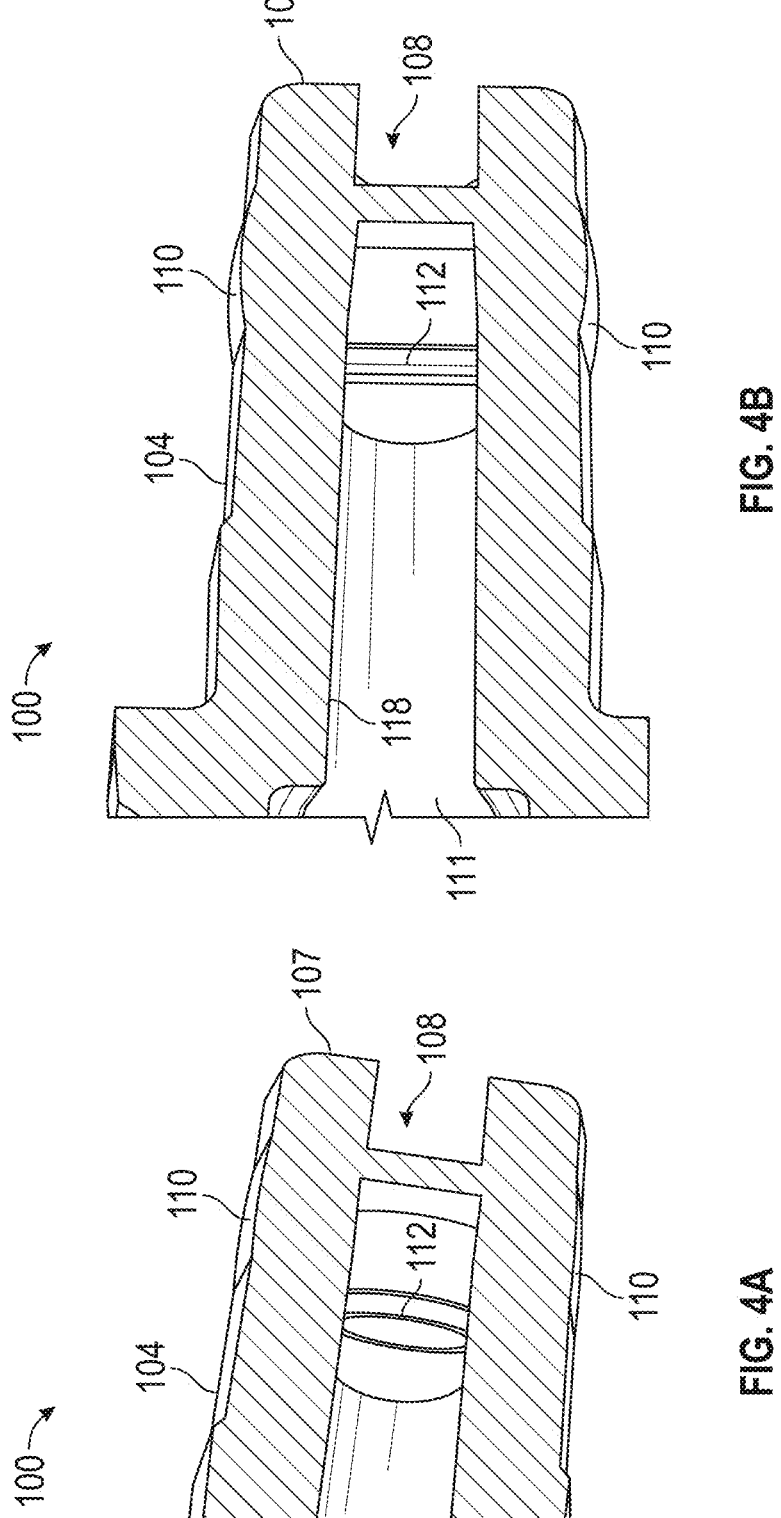
FIG. 4A illustrates a partial cross-sectional view of a male luer medical connector with valve member in an open position, in accordance with some embodiments of the present disclosure.
FIG. 4B illustrates a partial cross-sectional view of a male luer medical connector with valve member in a closed position, in accordance with some embodiments of the present disclosure.

FIG. 4A illustrates a partial cross-sectional view of a male luer medical connector with valve member in an open position, in accordance with some embodiments of the present disclosure. FIG. 4B illustrates a partial cross-sectional view of a male luer medical connector with valve member in a closed position, in accordance with some embodiments of the present disclosure. Referring to FIGS. 4A and 4B, with continued reference to FIGS. 2A-3B, an outer surface 110 of the compressible valve member 116 may extend to the exterior of the medical connector 100. The compressible valve member 116 may further include an inner surface, in which the slit 112 is defined. As depicted, the slit 112 may define at least a portion of a flow channel through the compressible valve member.

Figures 5A, 5B:
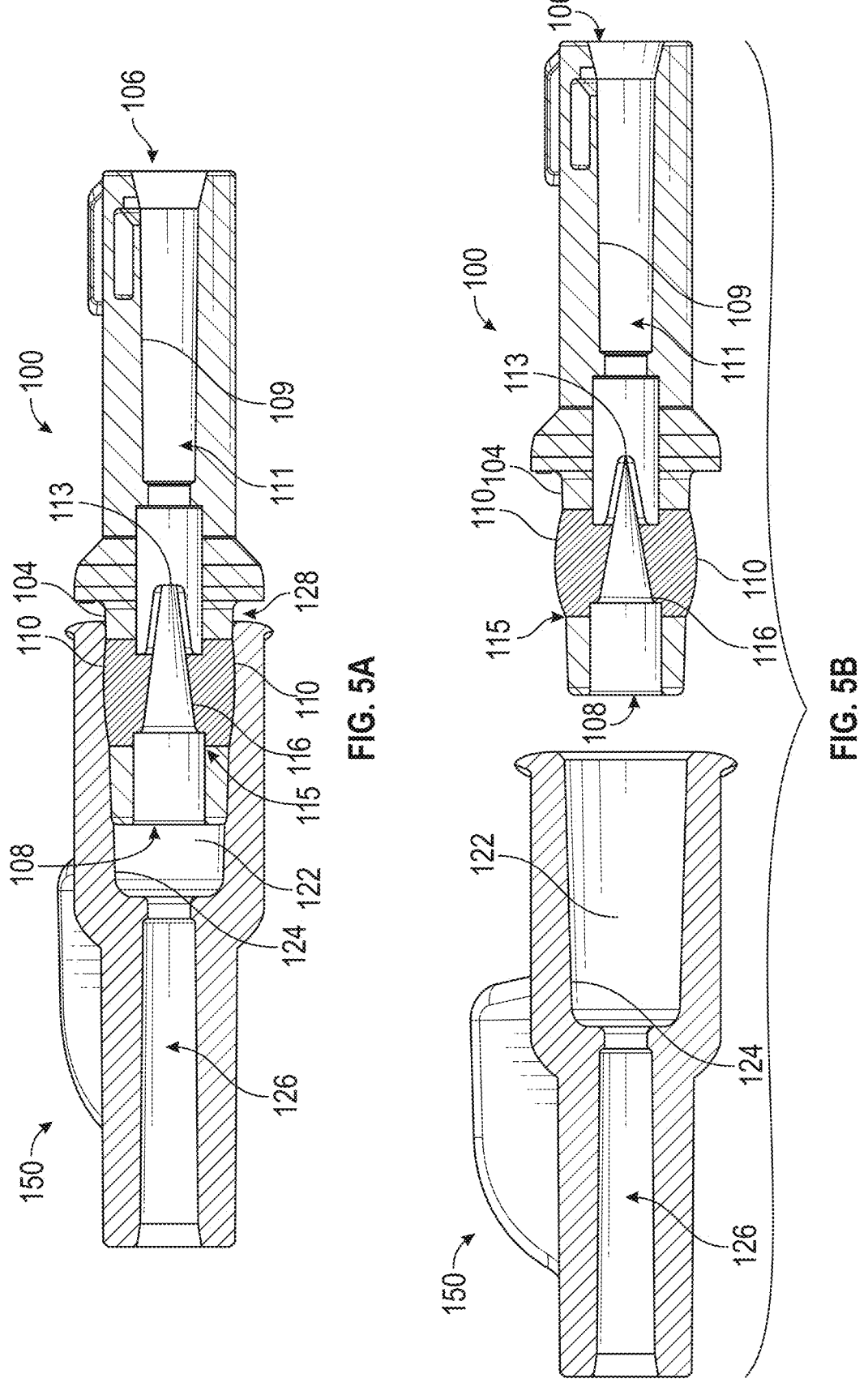
FIG. 5A illustrates a sectional view of a male luer medical connector having a compressible valve member in a connected state with a medical access device.
FIG. 5B illustrates a sectional view of a male luer medical connector having a compressible valve member in a disconnected state with a medical access device.

FIG. 5A illustrates a sectional view of a male luer medical connector having a compressible valve member in a connected state with a medical access device. FIG. 5B illustrates a sectional view of a male luer medical connector having a compressible valve member in a disconnected state with a medical access device. According to various embodiments of the present disclosure, the compressible valve member 116 may have a proximal end 113 and a distal end 115. As depicted in FIGS. 5A and 5B, the body of the compressible valve member may have a shape tapering from the distal end towards the proximal end. For example, in some embodiments, the compressible valve member may be a duckbill valve.

Referring to FIGS. 5A and 5B, with continued reference to FIGS. 3A-4B, the slit 112 may partition at least a portion of the body 118 of the compressible valve 116 into first and second valve sections 118A and 118B. In operation, as depicted in FIG. 5A, when the body 102 of the medical connector 100 is inserted into the medical access device 150, the first and second valve sections 118A and 118B are urged away from each other to open the slit 112. When the slit 112 is opened, the lumen 122 of the medical access device 150 and the lumen 111 of the medical connector 100 are fluidly communicated as the fluid path 126 between the fluid delivery sources or devices and the patient is opened.

In particular, since the outer surface 110 of the compressible valve member 116 may extend to the exterior of the medical connector 100 and protrude above the outer surface of the body 102, in the engaged state of the medical connector 100 and the medical access device 150, contact between outer surface 110 of valve member 116 and inner surface 124 of medical access device 150 exerts a force which causes compressible valve member 116 to be compressed radially inward so as to fit within the lumen 122 of the medical access device 150. As valve member 116 is compressed, the first and second valve sections 118A and 118B are biased away from each other, as illustrated in FIGS. 3A and 4A, to open the slit 112.

As the body 102 of the medical connector 100 continues to be inserted into medical access device 150, the first and second valve sections 118A and 118B continue to be biased away from each other until the slit is in a fully open position and formation of the fluid path 126 through connector 100 and medical access device 150 is completed. Although in the illustrated embodiments, connector 100 and medical access device 150 are illustrated as being securely attached by an interference fit, or a press fit, the various embodiments of the present disclosure are not limited to the aforementioned configuration. In some embodiments, connector 100 and medical access device 150 may be securely attached using complementary threads on the connector 100 and the medical access device.

Upon disconnection, as illustrated in FIG. 5B, removing connector 100 from medical access device 150 removes the compression force applied to the outer surface 110 of the compressible valve member 116, thereby allowing the compressible valve 116 to expand radially outward to its original uncompressed state. In particular, when the body 102 of the medical connector 100 is removed or disconnected from the medical access device 150 (as illustrated in FIG. 5B), the first and second valve sections 118A and 118B are biased towards each other to close the slit 112 (as illustrated in FIGS. 3B and 4B). When the slit 112 is in a fully closed position, the fluid path 126 through connector 100 and medical access device 150 is closed thereby blocking fluid communication between the connector 100 and medical access device 150.

While medical access device 150 is shown in the form of a female luer having a valve plug arrangement, connector 100 will work with any standard female luer of a medical access device including bellows type plugs, devices with septums, or other configurations designed to accept standardized male luer connectors such as the body 102 of the medical connector 100.

According to various embodiments of the present disclosure, a method of assembling a connector 100 may include the steps of providing a connector body 102 having an outer surface 104 and an inner surface 109 defining a lumen 111 of the connector body 102. The method may further include positioning a compressible valve member 116 comprising a normally closed slit 112 in the lumen 111 with an outer surface of the compressible valve member 116 extending through the inner and outer surfaces 109 and 104 of the connector body 102 to an exterior of the medical connector 100. In some embodiments, providing the connector body 102 further includes forming an inlet port 106 at a proximal end of the body and forming an outlet port 108 at a distal end of the body, and extending the lumen from the inlet port 106 to the outlet port 108 to define a fluid path between the inlet and outlet ports.

In some embodiments, a geometry of the outer surface of the connector body may be formed to comply with International Organization for Standardization (ISO) standards.

The medical connector 100 of the various embodiments described herein may differ from a traditional male luer connector by the inclusion of a compressible valve member including a normally closed slit and a body having an outer surface which extends through the inner and outer surfaces of the medical connector body to an exterior of the medical connector. The compressible valve member may be advantageously configured (i) to compress radially inward to open the slit upon insertion of the body into a medical access device, and (ii) to expand radially outward to close the slit upon disconnection of the body from the medical access device. Accordingly, the medical connector of the various embodiments described herein may advantageously close the fluid path when disconnected from a medical access device in order to prevent dripping or leakage of medical fluid which is a common issue occurring upon disconnection of the currently existing medical connectors (e.g., male luer) from the medical access devices. Further advantageously, the auto shut off medical connector of the various embodiments described herein may allow the clinician to simply disconnect without having to physically close all clamps to prevent a free flow leak state.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A medical connector comprising: a body having an outer surface and an inner surface defining a lumen of the body; an inlet port defined at a proximal end of the body, and an outlet port defined at a distal end of the body; and a compressible valve member comprising a normally closed slit and disposed in the lumen and extending through the inner and outer surfaces of the body to an exterior of the medical connector, wherein the compressible valve member is configured to compress radially inward to open the slit upon insertion of the body into a medical access device, and the compressible valve member is configured to expand radially outward to close the slit upon disconnection of the body from the medical access device.

Clause 2. The medical connector of Clause 1, wherein the compressible valve member comprises a body having an outer surface extending to the exterior of the medical connector, and the slit comprises an inner surface defining a flow channel through the body of the compressible valve member.

Clause 3. The medical connector of Clause 2, wherein the body of the compressible valve member comprises a proximal end and a distal end, the body of the compressible valve member having a shape tapering from the distal end towards the proximal end.

Clause 4. The medical connector of Clause 2, wherein the slit partitions at least a portion of the body of the compressible valve member into first and second valve sections, and when the body of the medical connector is inserted into the medical access device, the first and second valve sections are urged away from each other to open the slit.

Clause 5. The medical connector of Clause 4, wherein the outer surface of the body of the compressible valve member is compressed radially inward by an inner surface of the medical access device to bias the first and second valve sections away from each other and open the slit.

Clause 6. The medical connector of Clause 4, wherein when the body of the medical connector is removed or disconnected from the medical access device, the first and second valve sections are biased towards each other to close the slit.

Clause 7. The medical connector of Clause 6, wherein the outer surface of the body of the compressible valve member is expanded radially outward when the body of the medical connector is removed or disconnected from an inner surface of the medical access device to bias the first and second valve sections toward each other and close the slit.

Clause 8. The medical connector of any one of Clauses 1 to 7, wherein the compressible valve member comprises an elastomeric material.

Clause 9. The medical connector of Clause 8, wherein the elastomeric material comprises silicone, Thermoplastic Polyurethane (TPU), or a combination thereof.

Clause 10. The medical connector of any one of Clauses 1 to 9, wherein the compressible valve member comprises a duckbill valve.

Clause 11. A method of assembling a medical connector, the method comprising the steps of: providing a connector body having an outer surface and an inner surface defining a lumen of the connector body; and positioning a compressible valve member comprising a normally closed slit in the lumen with an outer surface of the compressible valve member extending through the inner and outer surfaces of the connector body to an exterior of the medical connector.

Clause 12. The method of Clause 11, wherein providing the connector body further comprises forming an inlet port at a proximal end of the connector body and forming an outlet port at a distal end of the connector body, and extending the lumen from the inlet port to the outlet port to define a fluid path between the inlet and outlet ports.

Clause 13. The method of any one of Clauses 11 and 12, wherein providing the connector body further comprises forming a geometry of the outer surface of the connector body to comply with International Organization for Standardization (ISO) standards.

Clause 14. The method of any one of Clauses 11 to 13, wherein positioning the compressible valve member comprises positioning a compressible valve member formed of an elastomeric material in the lumen.

Clause 15. The method of Clause 14 wherein positioning the compressible valve member comprises positioning a compressible valve member formed of silicone, Thermoplastic Polyurethane (TPU), or a combination thereof in the lumen.

Clause 16. A connector assembly, comprising: a female luer comprising an outer surface and an inner surface defining a lumen of the female luer; and a male luer removably disposed at least partially in the lumen of the female luer, the male luer comprising: a body having an outer surface and an inner surface defining a lumen of the body; and a compressible valve member disposed in the lumen and extending through the inner and outer surfaces of the body, the compressible valve member having an outer surface and an inner surface comprising a slit, wherein: the inner surface of the female luer compresses at least a portion of the outer surface of the compressible valve member to open the slit when the male luer is disposed in the female luer; and upon removal from the female luer, the compressible valve member expands radially outward to close the slit.

Clause 17. The connector assembly of Clause 16, wherein the slit partitions at least a portion of the compressible valve into first and second valve sections, and when the body of the male luer is inserted into the female luer, the first and second valve sections are urged away from each other to open the slit.

Clause 18. The connector assembly of Clause 17, wherein when the body of the male luer is removed or disconnected from the female luer, the first and second valve sections are biased towards each other to close the slit.

Clause 19. The connector assembly of any one of Clauses 16 to 18, wherein the compressible valve member comprises an elastomeric material.

Clause 20. The connector assembly of Clause 19, wherein the elastomeric material comprises silicone, Thermoplastic Polyurethane (TPU), or a combination thereof.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A medical connector comprising:

a body having an outer surface, an inner surface, an inlet port defined at a proximal end of the body, an outlet port defined at a distal end of the body, the inner surface defining a fluid lumen of the body between the inlet port and the outlet port, and an opening extending from the inner surface to the outer surface of the body; and a compressible valve member disposed in the lumen of the body and comprising a normally closed slit and an outer surface with a portion that extends through the opening from the lumen of the body to the outer surface of the body, wherein the portion of the compressible valve member that extends through the opening is configured to compress radially inward to open the slit upon insertion of the body into a medical access device, and the portion of the compressible valve member is configured to expand radially outward to close the slit upon disconnection of the body from the medical access device.

2. The medical connector of claim 1, wherein the compressible valve member comprises a body, and the slit comprises an inner surface defining a flow channel through the body of the compressible valve member.

3. The medical connector of claim 2, wherein the body of the compressible valve member comprises a proximal end and a distal end, and a shape tapering from the distal end of the body of the compressible valve member towards the proximal end of the body of the compressible valve member.

4. The medical connector of claim 2, wherein the slit partitions at least a portion of the body of the compressible valve member into first and second valve sections, and when the body of the medical connector is inserted into the medical access device, the first and second valve sections are urged away from each other to open the slit.

5. The medical connector of claim 4, wherein the outer surface of the compressible valve member is configured to be compressed radially inward by an inner surface of the medical access device to bias the first and second valve sections away from each other and open the slit.

6. The medical connector of claim 4, wherein when the body of the medical connector is removed or disconnected from the medical access device, the first and second valve sections are biased towards each other to close the slit.

7. The medical connector of claim 6, wherein the outer surface of the compressible valve member is expanded radially outward when the body of the medical connector is removed or disconnected from an inner surface of the medical access device to bias the first and second valve sections toward each other and close the slit.

8. The medical connector of claim 1, wherein the compressible valve member comprises an elastomeric material.

9. The medical connector of claim 8, wherein the elastomeric material comprises silicone, Thermoplastic Polyurethane (TPU), or a combination thereof.

10. The medical connector of claim 1, wherein the compressible valve member comprises a duckbill valve.

* * * * *